(12) United States Patent
Grun et al.

(10) Patent No.: US 7,760,354 B2
(45) Date of Patent: Jul. 20, 2010

(54) SPECTROSCOPIC METHOD AND APPARATUS FOR IDENTIFICATION OF A SUBSTANCE USING A TUNABLE LIGHT SOURCE

(75) Inventors: Jacob Grun, Silver Spring, MD (US); Sergei Nikitin, Springfield, VA (US); Charles K Manka, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/248,272

(22) Filed: Oct. 9, 2008

(65) Prior Publication Data

US 2009/0086205 A1 Apr. 2, 2009

Related U.S. Application Data

(63) Continuation-in-part of application No. 11/946,762, filed on Nov. 28, 2007, now Pat. No. 7,436,510, which is a continuation of application No. 11/031,945, filed on Jan. 7, 2005, now abandoned.

(51) Int. Cl.
*G01N 21/63* (2006.01)
*G01N 21/64* (2006.01)
*G01N 21/65* (2006.01)

(52) U.S. Cl. .................. 356/318; 356/301; 356/307; 250/458.1

(58) Field of Classification Search ................. 356/317, 356/318
See application file for complete search history.

(56) References Cited

U.S. PATENT DOCUMENTS 4,620,284 A * 10/1986 Schnell et al. .............. 702/28
4,642,778 A * 2/1987 Hieftje et al. .............. 702/23
5,479,255 A * 12/1995 Denny et al. .............. 356/319

* cited by examiner

*Primary Examiner*—F. L Evans
(74) *Attorney, Agent, or Firm*—Amy Ressing; L. George Legg

(57) ABSTRACT

A spectroscopic detector includes a tunable light source, such as a continuously tunable, optical parametric oscillator laser; means for measuring the emitted radiation at a plurality of emission wavelengths to obtain a plurality of spectral measurement data; and a processor for processing the spectral measurement data, where the processor includes a multispectral data processing algorithm or is configured for 1) combining the plurality of spectral measurement data into a composite spectrum, and 2) applying the algorithm to the composite spectrum. The spectra such as resonant and near-resonant Raman Spectra that are acquired are more complete and contain more information. A powerful multispectral analysis code such as IHPS, CHOMPS, or ENN analyzes the acquired data points, examining details of the spectra that could not be handled by traditional methods.

22 Claims, 13 Drawing Sheets

SPECTROSCOPIC METHOD AND APPARATUS FOR IDENTIFICATION OF A SUBSTANCE USING A TUNABLE LIGHT SOURCE

CROSS-REFERENCE TO RELATED APPLICATIONS

The present application is a continuation-in-part of U.S. patent application Ser. No. 11/946,762, filed Nov. 28, 2007, now U.S. Pat. No. 7,436,510 which is a continuation of U.S. patent application Ser. No. 11/031,945, filed Jan. 7, 2005 now abandoned.

FIELD OF THE INVENTION

This invention relates to a method and apparatus for identifying a substance either in or without the presence of other substances. More particularly, the invention relates to a method and apparatus employing a tunable light source for identifying chemical, biological or other constituents of interest in or without the presence of other substances.

BACKGROUND OF THE INVENTION

Spectroscopic identification of bio-organisms utilizing resonance or near-resonance-Raman spectroscopy, described in U.S. Pat. No. 4,847,198, incorporated herein by reference, is a method through which biological organisms are identified from the highly structured emission spectra resonantly excited by illumination with Deep UltraViolet, ~0.2-0.3 micron, (DUV) radiation. FIG. 1 illustrates the prior art system described in U.S. Pat. No. 4,847,198. A light source 12 comprises a laser 14, e.g. a Nd-Yag device, producing high energy light pulses at 1064 nm, 532 nm, 355 nm, and 266 nm; a dye laser 16, e.g. a Quanta-Ray PDL-2 which shifts pulse energies from Yag frequencies to lower energies; and a wavelength extender 18 that either doubles the dye laser output or mixes the dye-laser output or doubled dye laser output with an Nd-Yag fundamental to produce pulsed UV light at a wavelength between 350-216 nm. The output from the wavelength extender 18 strikes a split prism 20 which produces two beams. A first reference beam strikes a mirror and is reflected onto a photodiode 22. The output from the photodiode is transmitted to a Princeton Applied Research Model 162 Boxcar Averager 24. A Spex Datamate DMO1 microcomputer 26 controls the stepping motor (not illustrated) of a monochromator 40, for general data acquisition and disc storage of spectra. The second beam from the prism 20 strikes a mirror 28 which directs the beam to a sample 30 under investigation. The energy backscattered from the sample is collimated by a lens 32, condensed by an optically aligned lens 34 and focused by the lens 34 on an entrance slit of the monochromator 40. In this manner, a single wavelength in the UV or DUV range illuminates the sample and backscattered energy, i.e. resonance or near-resonance enhanced Raman scattering, or Raman scattering from a microorganism with a characteristic spectrum or "fingerprint", is collected.

FIGS. 2a and b show the highly structured spectra of identifiable biological organisms resonantly excited by illumination of the sample to be examined with deep ultraviolet, ~0.2-0.3 micron, (DUV) light. FIG. 2a shows spectra from *Pseudomonas fluorescens* (top), *E. coli* (second from top), *Bacillus subtilis* (third from top), and *Staphylococcus epidermidis* (bottom) illuminated by a single DUV wavelength. The spectra contain a few large peaks. Prior-art authors attempted to use the locations of the large peaks for identification. We observe that the peaks have different shapes, that the spectra are very structured and visibly different for each organism observed. With proper analysis techniques, therefore, the entire spectrum can be used to make identification. FIG. 2b shows spectra from *B. megaterium* spores illuminated at widely separated times by 4 different DUV wavelengths. Prior-art authors note that different illumination wavelengths produce major peaks at similar locations. We, however, observe that each individual illumination wavelength produces a spectrum that differs in features other than the major peak location, thus adding to the information that comprises the organism's signature. The spectra originate from resonant and near-resonant interactions of the illuminating DUV light with chemical bonds within and among nucleic and amino acids that constitute more than 50% (by dry weight) of the organism's mass. Hence, the spectra constitute a (partial) fingerprint of the organism. Because the light is in the DUV region the bond interaction is near-resonant, the Raman scattering is enhanced with signal-to-noise ratios of $10^3$-$10^4$ being typical. In previous studies, spectra, with signal-to-noise sufficient for analysis, from as few as 20 organisms in a clean environment measured in 15 seconds have been demonstrated. Very importantly for biological measurements, interference from broad-band fluorescence in the DUV region of the spectrum where this method operates is virtually non-existent. The illuminating light need not damage the sample, allowing confirmation of positive readings through immediately repeated measurements by the same instrument. The sample can also be saved for forensic examination by other techniques at a later time. In addition, the spectra have been shown to contain information about the organism's stage of development and other information useful for assessing the threat posed by the organism.

This prior art technique has very limited ability to identify species. The ability to distinguish gram+ from gram– bacteria has been demonstrated, but more specific identification has not been possible. Even this crude level of identification has been demonstrated in pure samples only, not when the substance of interest is present along with other substances. Excitation at a single wavelength may excite not just the substance of interest but also some or all of the other substances present, spectrally masking its signature and making it difficult to interpret the emitted spectra and to identify the substance of interest.

Other approaches have applied spectral data processing algorithms to data resulting from a single illumination wavelength of pure samples but have demonstrated only a limited capability to distinguish between spectral "fingerprints", that is, the ability to identify a signature of a particular species, organism, or substance. None have been successful identifying an organism in the presence of other substances and/or organisms. Some require obtaining sets of training data and do not therefore lend themselves effectively to real time processing needs. Others exhibit limited ability to identify organisms due to the inherent limitations of their spectral data processing methodology.

Other current identification technologies, such as PCR, require a pre-enrichment step—i.e., a step in which the organism to be identified is grown for hours or days to provide the large number of organisms required for the identification method to be effective.

There is a need for a substance detector that can identify substances in the presence of or without (e.g. a pure culture) other substances, to do so rapidly, and to do so with high sensitivity, and specificity, for example, identifying a minimal number of an organism in the presence of other organisms, or in a pure culture.

SUMMARY OF THE INVENTION

According to the invention, a method of identifying the presence of a first substance in the presence of at least one other substance includes illuminating the first substance and the at least one other substance with a laser output from a continuously tunable, optical parametric oscillator laser (or another type of tunable laser or tunable light source)to thereby induce the emission of radiation characteristic of the substances being illuminated; measuring the emitted radiation to obtain a plurality of spectral measurement data; and inputting the spectral measurement data into a processor.

In one embodiment, the processor includes a processing algorithm configured for 1) combining the plurality of spectral measurement data into a composite spectrum, and 2) applying the algorithm to the composite spectrum whereby at least one parameter characteristic of the first substance is identified while information in the composite spectrum contributed by an emission of radiation from the at least one other substance is removed to thereby identify the presence of the first substance.

In another embodiment, the processor includes a multispectral data processing algorithm for identifying at least one parameter characteristic of the first substance while removing information contributed by an emission of radiation from the at least one other substance to thereby identify the presence of the first substance.

Particular embodiments of methods to illuminate a sample at a plurality of wavelengths include a continuously tuned laser, such as a laser based on the optical parametric oscillator laser, or a laser based on broad-band Titanium Sapphire oscillator technology, or another tunable light source. In these embodiments, the invention overcomes the prior art limitations noted above by acquiring spectra, preferably resonant and near-resonant Raman Spectra, that are more complete and contain more information. It also overcomes prior art limitations noted above by utilizing a powerful code to analyze the information contained in these spectra. For example, in an application in which one hundred different illumination wavelengths are used, the acquired spectra contain as much as 100 times the information of the traditional single illumination wavelength Raman spectrum. This provides an increase of specificity and a greater resistance to interference from background clutter. The embodiment requires no pre-enrichment or only minimal pre-enrichment.

A powerful multispectral analysis code such as IHPS, CHOMPS, or ENN analyzes every acquired data point, examining details of the spectra that could not be handled by traditional methods. Here, multispectral is meant to indicate a number of wavelength dependent measurements greater than one. It is not meant to limit the number of such measurements in any way, although, in practice that number will typically be much greater than 1. Important features of multispectral processors are their speed, their ability to distinguish between spectral "fingerprints" that cannot be reliably identified by conventional methods, the ability to identify a signature of a small amount of an organism in a high background clutter, and the ability to store microorganisms' spectral signatures in a built-in library.

The invention provides a new tool with which to study the protein or DNA/RNA markers of microorganisms and cells, as well as a tool to rapidly identify and count organisms that cause diseases. The invention also provides a tool to identify compounds, including chemicals in the presence of other chemicals. Specific applications include air monitoring, water monitoring, monitoring during food production, monitoring during production of pharmaceuticals, rapid detection of targeted disease organisms such as tuberculosis, pre and post sterilization monitoring, monitoring of allergens, identification of folded proteins (prions), identification of forgeries, identifying contaminated materials, and monitoring of blood constituents.

The invention also identifies a substance in a pure culture or other similar applications where another substance is not present.

Additional features and advantages of the present invention will be set forth in, or be apparent from, the detailed description of preferred embodiments which follows.

DETAILED DESCRIPTION OF THE PREFERRED EMBODIMENTS

Figure 1:
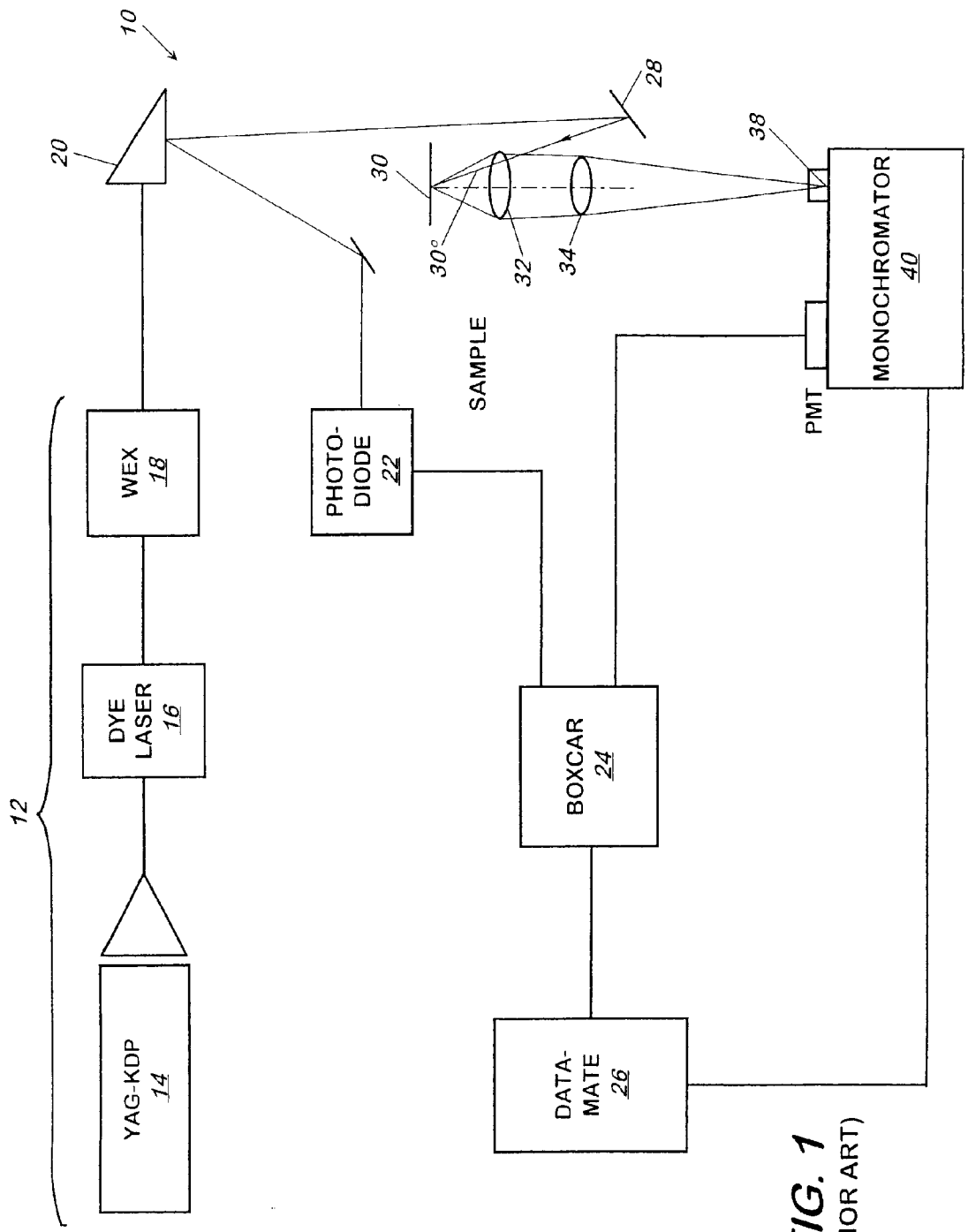
FIG. 1 is a schematic representation of a prior art resonance Raman UV detection system.
Figure 2A:
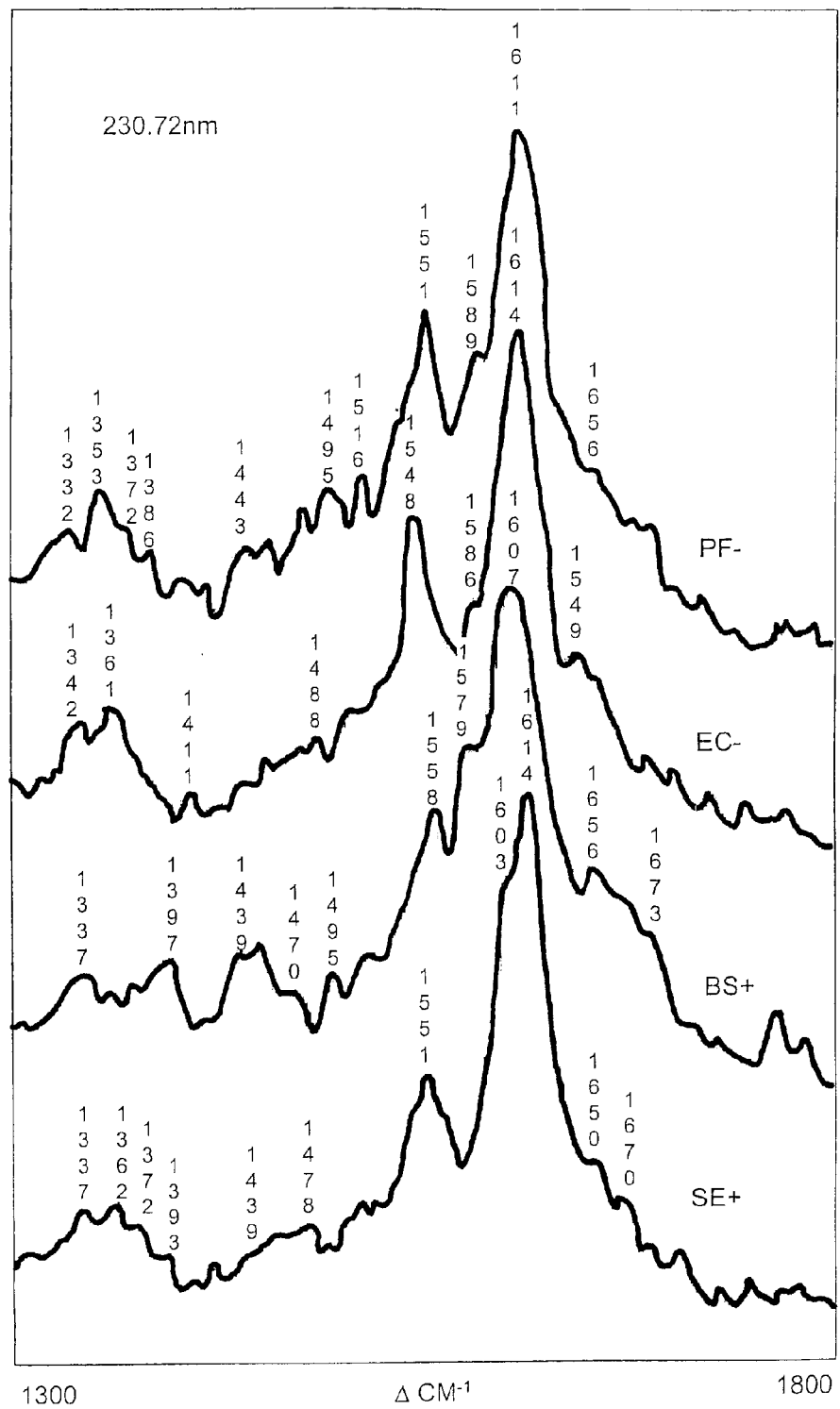
FIGS. 2a and b are spectral graphs of biological organisms resonantly excited by illumination of a sample with DUV light.
Figure 2B:
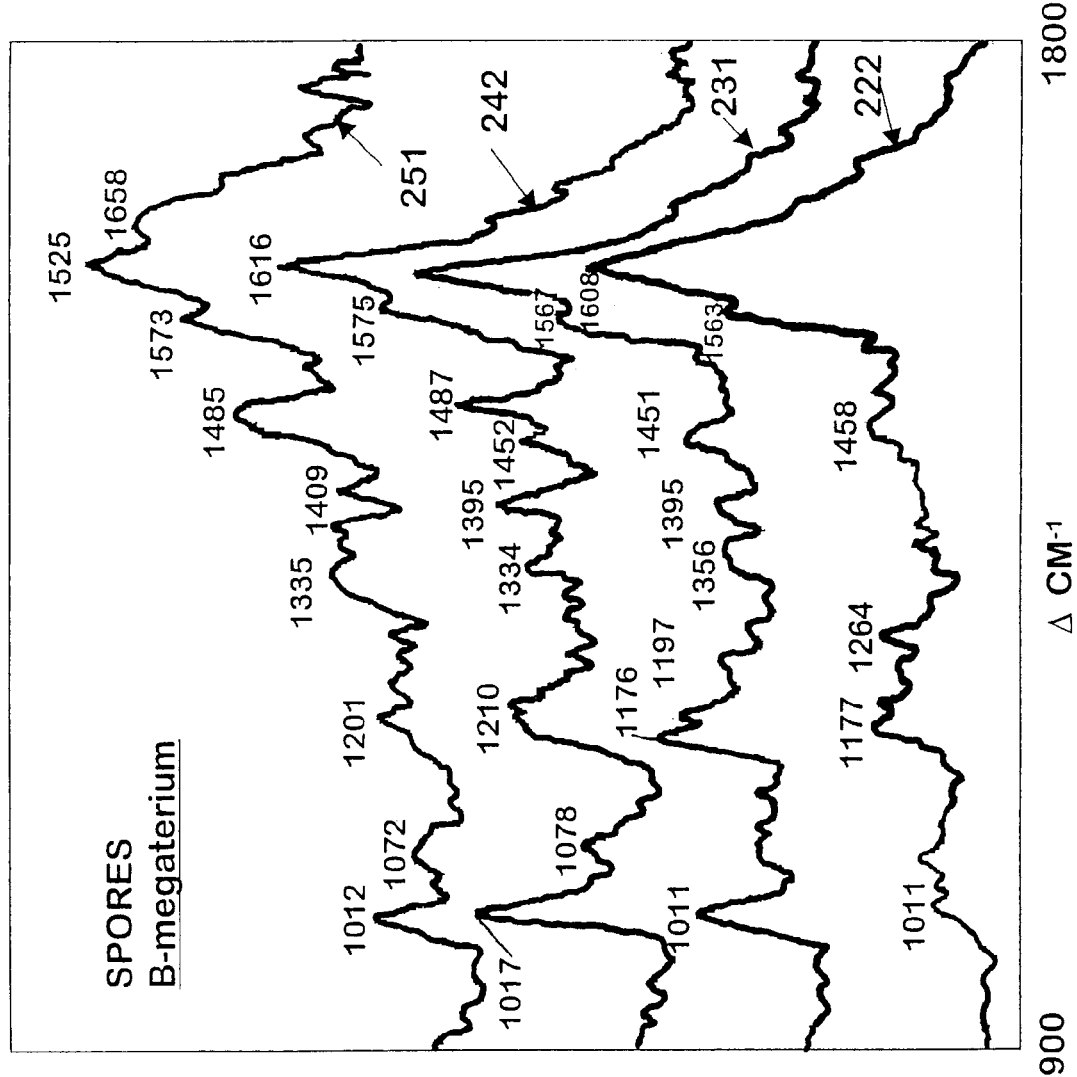
Figure 3:
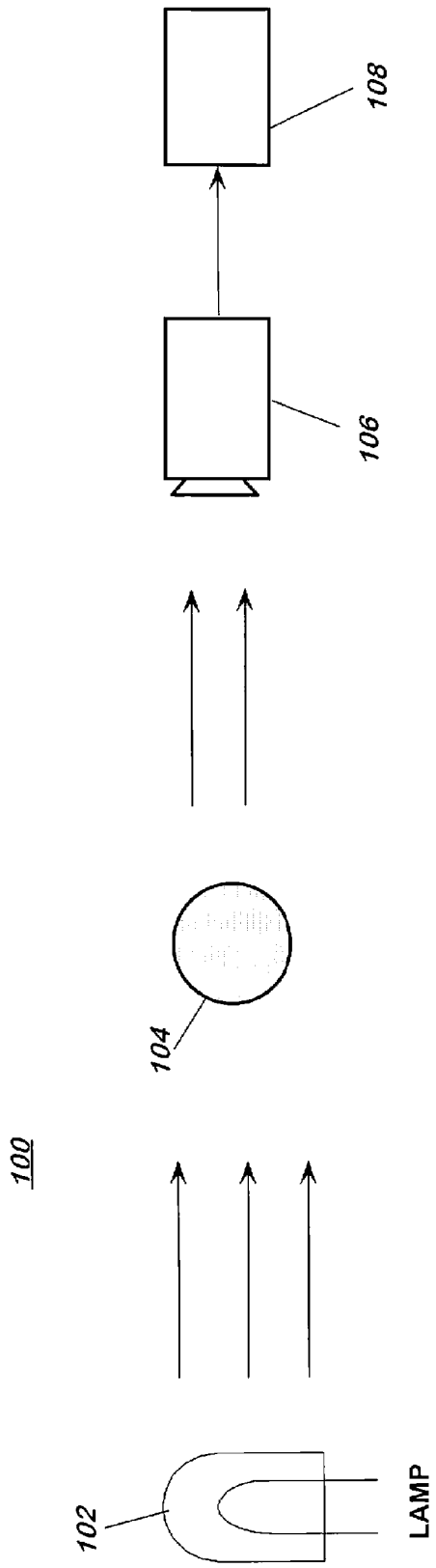
FIG. 3 is a schematic diagram of a spectroscopic detector according to the invention.

Referring now to FIG. 3, a spectroscopic detector 100 includes an illumination source 102 for illuminating a sample 104 and thereby inducing the emission of radiation characteristic of the sample, a spectrum acquisition sensor or sensors 106 for sensing and capturing as spectral measurement data the response spectrum in the emitted radiation, and a processor 108 for processing and analyzing the spectral measurement data.

Source 102 includes a number of options, as follows:

Laser Illuminator (Type 1):

A single Gain Module, pumped by a pair of 40-W diode bars. Combined with the second-harmonic unit, this can generate about 10 W of average power at a 5-kHz rate. The Ti:sapphire laser pumped by this, tuned to 800 nm, produces an average power of 4 W.

The 700-960 nm UV light from the Ti:sapphire laser is tripled or quadrupled to the DUV 233-320 nm using BBO (Beta Barium Borate) crystals. This nonlinear material, beta-barium borate (BaB2O4), has a large birefringence and UV transparency to 200 nm, allowing it to serve multiple roles as a doubler, tripler, or quadrupler of the fundamental Ti:sapphire wavelengths. For proper frequency multiplication, as the Ti:sapphire wavelength is tuned, the angles for the BBO crystals must be adjusted accordingly. An internal diagnostic and feedback loop automatically adjusts the angle of the BBO nonlinear crystals to maximize conversion efficiency as the wavelength of the laser is changed.

Figure 4:
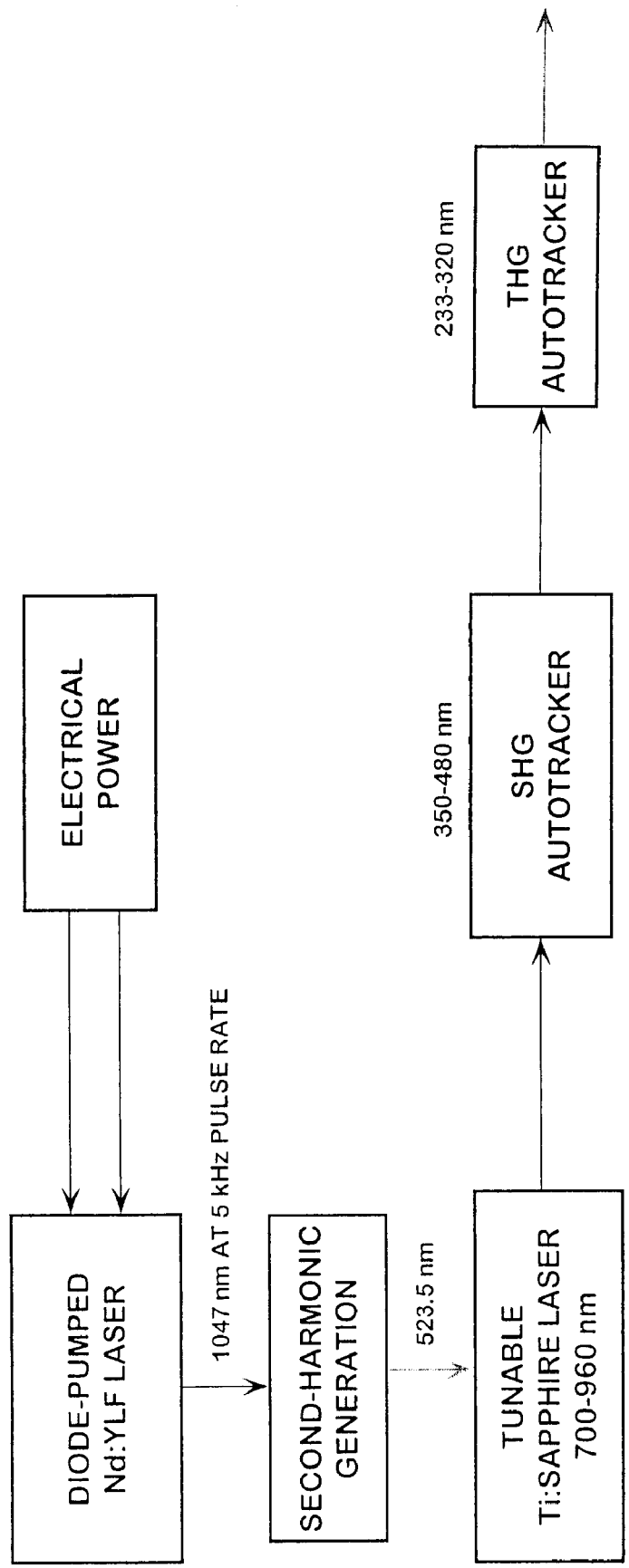
FIG. 4 is a block diagram of an integrated DUV illuminator for diode-pumped lasers according to the invention.

FIG. 4 presents a block diagram of an integrated DUV illuminator for diode-pumped lasers that includes a Nd:YLF laser pump, power supply and second-harmonic generation blocks. The Ti:sapphire laser tuning is accomplished by rotation of a three-plate birefringent filter driven by a computer-controlled stepper motor (not illustrated). The harmonic-generation process for the Ti:sapphire laser uses two BBO crystals mounted in Inrad Autotracker III units and generates UV average powers at the 10-100 mW level.

Laser Illuminator (Type 2)

Recent developments in optical-fiber technology make it possible to replace the diode-pumped Nd:YLF laser with a fiber laser. For example, the fiber-amplifier output can be in the form of pulses, with sub-ns duration, at a pulse rate of several kHz and per-pulse energy of hundreds of mJ, leading to an average power of more than 1 W. A fiber amplifier is highly efficient,. With high peak power pulses one can double the fiber-laser output frequency with high efficiency using nonlinear crystals.

There are several advantages in using the fiber-laser design:
No active cooling is needed for the fiber medium.
The diode-pump absorption band for the fiber is broad, relaxing any temperature-control requirements for the diode pump lasers
The microchip laser is monolithic, eliminating any cavity mirrors that could go out of alignment.
The overall pump laser hardware occupies a small volume, allowing construction of a compact system.

A Ti:sapphire laser employs a short resonator and produces sub-ns pulses. The threshold for the Ti:sapphire laser is 30 mJ, the slope efficiency is 45% at the operating wavelength of 780 nm and the line width is 170 pm. The short pulses from this laser are ideal for driving the harmonic-generation process. A further reduction in line width is required to fall within the spectral acceptance of the nonlinear crystals best suited for DUV generation. This is accomplished through the use of higher-finesse tuning elements.

Laser Illuminator (Type 3)

Light source 102 is a tunable light source, e.g. a tunable laser such as a tunable optical parametric oscillator (OPO) laser source pumped by the third harmonic of a Nd laser, from which the fundamental wavelengths, or frequency doubled or tripled wavelengths are extracted, e.g. the model PG 122/UV manufactured by EKSPLA Lasers and Laser Systems Div., Savanoriu, Lithuania, capable of generating fast optical pulses of about 5 nanosecond duration at about a 1 KHz frequency, continuously tunable from about 210 nm-320 nm, 400 nm-640 nm, and 710 nm-2100 nm. Tuning the laser to a desired wavelength is computer controlled and synchronized with the angular positions of gratings in the spectrometers and typically takes less than one second, enabling rapid data acquisition, processing, and data output in real time. The average power in the UV range is on the order from about 15 mW to about 70 mW. In the visible frequency range the power varies from 350 mW to 800 mW, and in the infrared the power is about 100 mW.

Monochromator Illuminator

Figure 5:
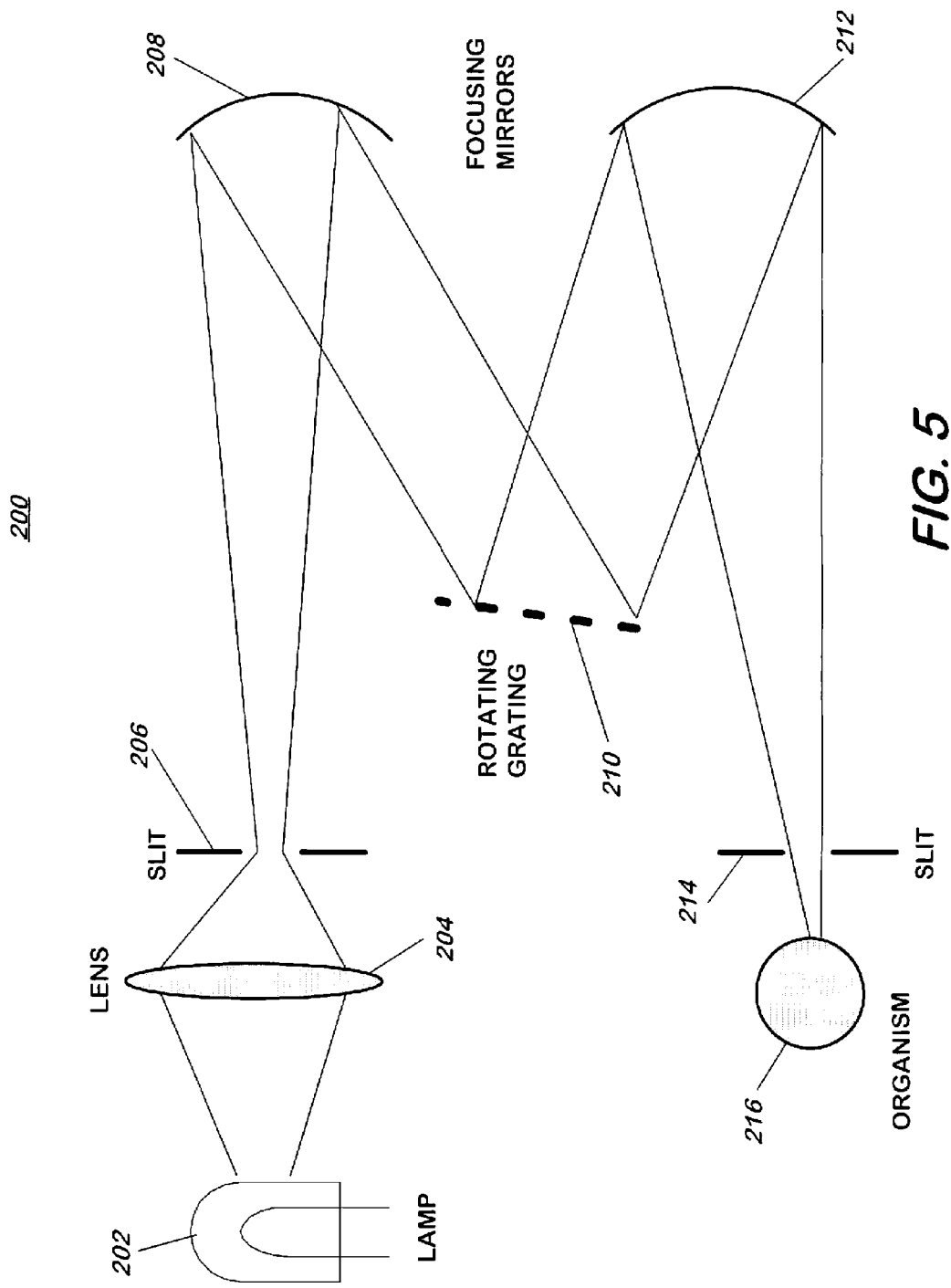
FIG. 5 is a schematic diagram of a monochromator type of spectrometer according to the invention.
Figure 6A:
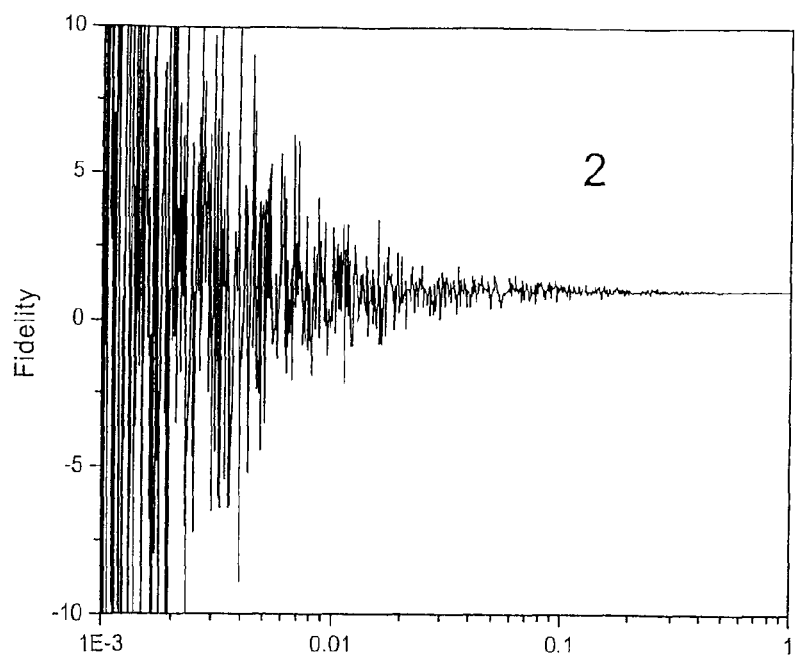
FIGS. 6a-c are graphs showing the performance of the detector employing the CHOMPS processing algorithms in calculating the amount of a BC bacterium hidden among EC bacteria and random noise, for signal to noise ratios of 2, 37, and 450, respectively, according to the invention.
Figure 6B:
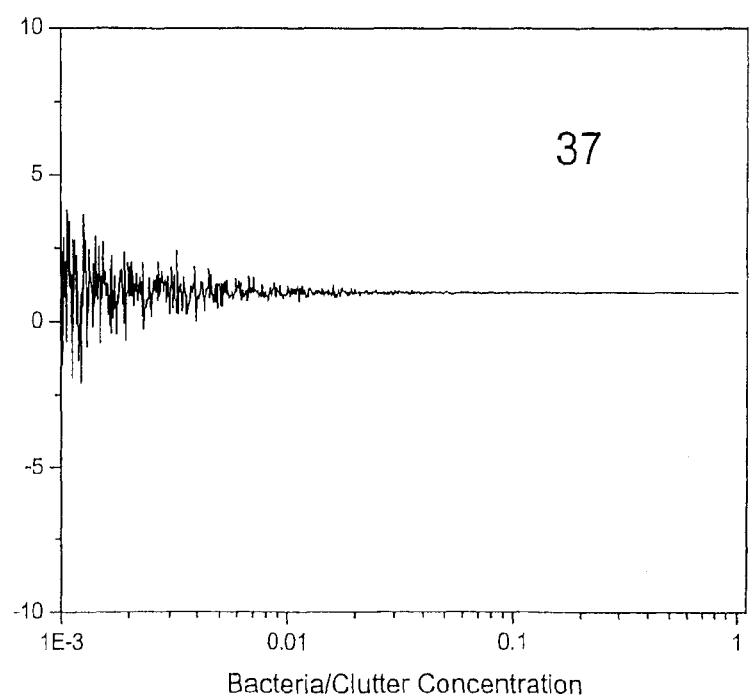
Figure 6C:
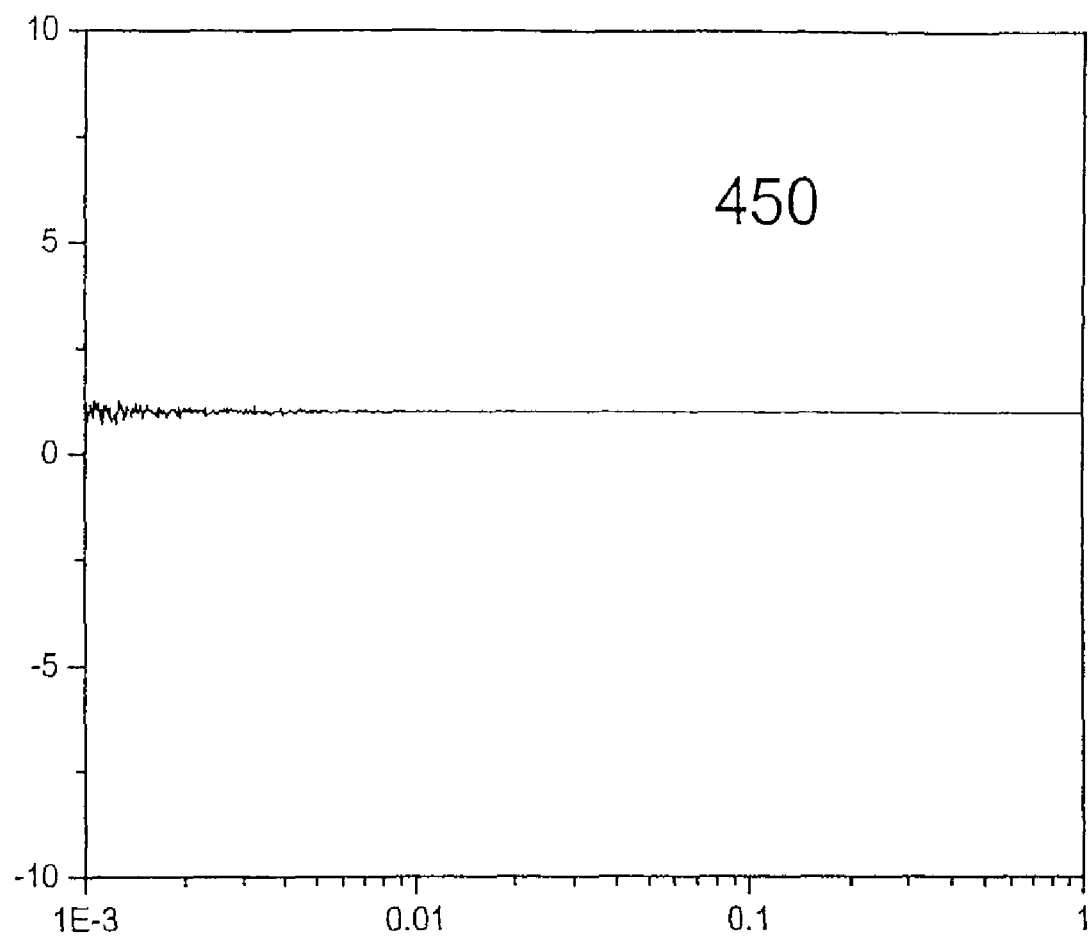
Figure 7:
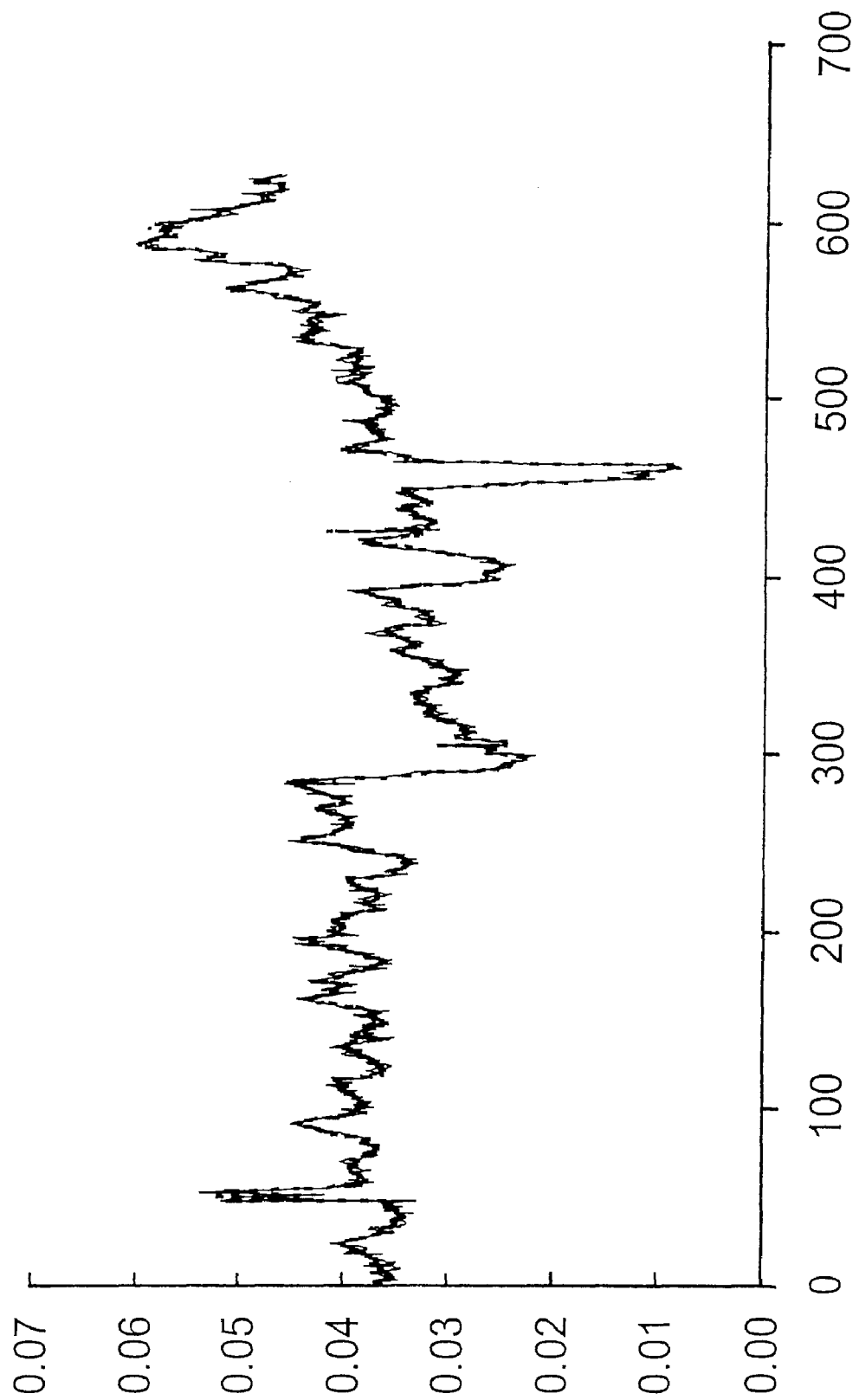
FIG. 7 is a graph showing an original measured spectrum and the spectrum plus a normally distributed noise for the BC-EC bacterial mixture of FIGS. 6a-c.
Figure 8:
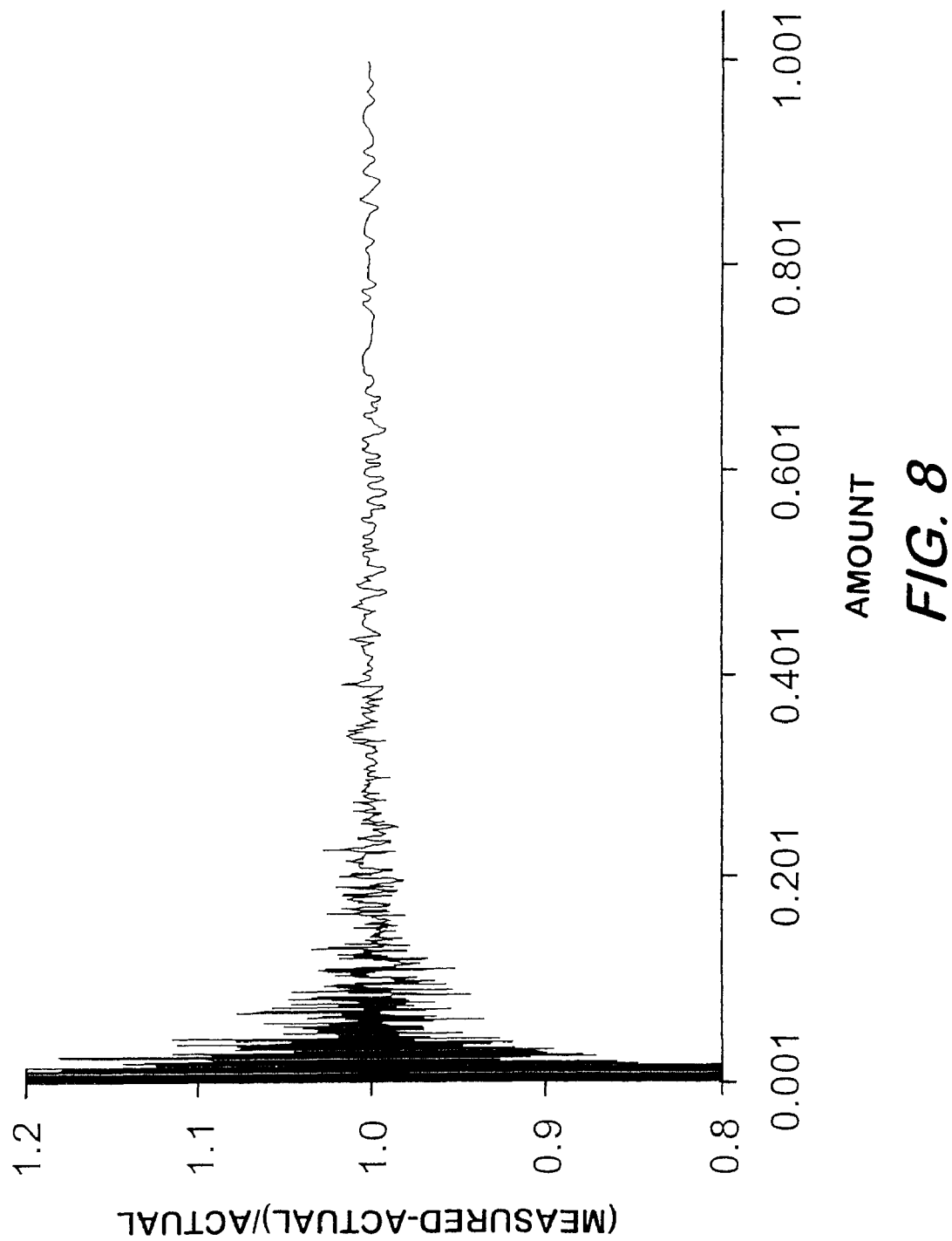
FIG. 8 is a graph showing the performance of the detector as in FIGS. 6a-c when only using one of the illuminating laser wavelengths according to the invention.
Figure 9:
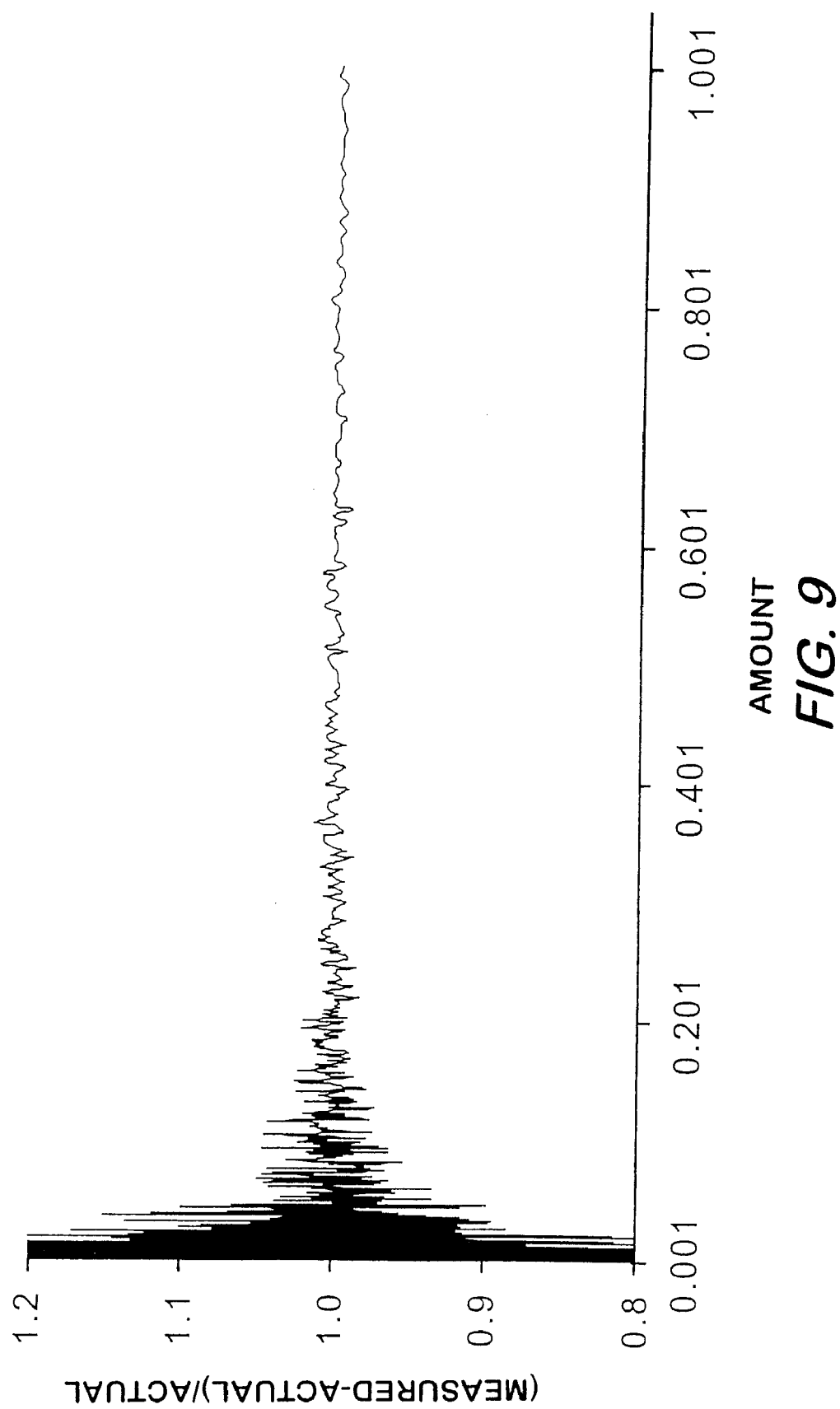
FIG. 9 is a graph showing the performance of the detector as in FIGS. 6a-c when using two of the illuminating wavelengths according to the invention.
Figure 10:
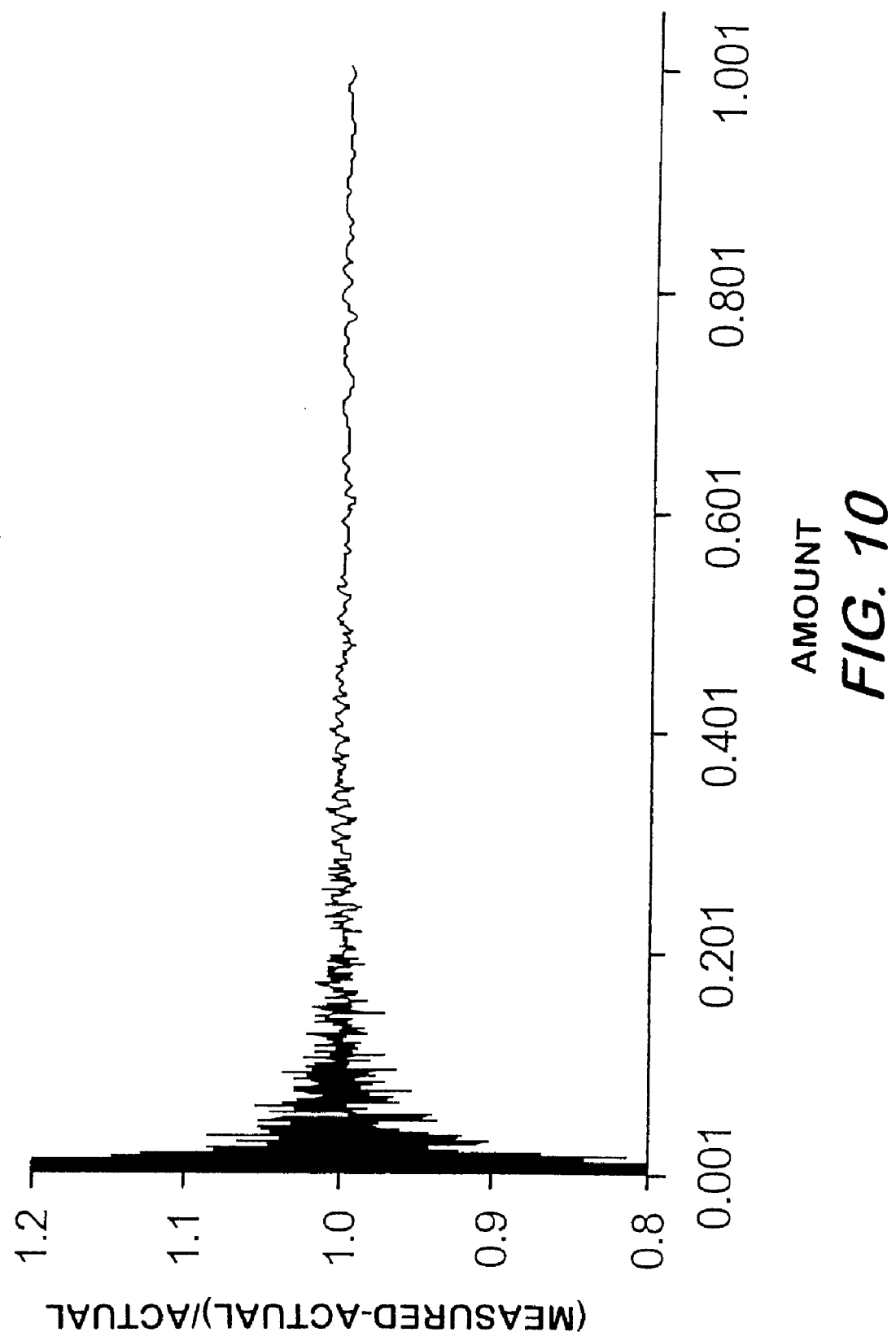
FIG. 10 is a graph showing the performance of the detector as in FIGS. 6a-c when using four of the illuminating wavelengths according to the invention.

The invention may alternatively employ a monochromator and a non-laser source, such as a deuterium lamp, for the illumination part of the system. A monochromator is a spectrometer whose output is a narrow wavelength band selected from a source containing a broader range of wavelengths or a number of distinct wavelengths. A monochromator can typically be scanned though large wavelength ranges by rotating a grating. FIG. 5 shows one common form of a monochromator 200 called the Cherny-Turner monochromator. Light from a broad-band source 202, such as a lamp, is focused by a lens 204 onto a variable-gap slit 206 and reflected by a concave mirror 208 onto a rotating grating 210. The grating 210 selects a narrow wavelength band from the many wavelengths that the source 202 produces. A second mirror 212 relays light at the selected wavelength band through a second slit 214 and a lens (not illustrated) onto the biological sample 216. Different wavelength bands can be selected sequentially by rotating the grating.

Illuminator Made from Composite Single-wavelength Subsystems

Illumination at a few laser wavelengths can be provided by monochromatic sources, such as excimer lasers or solid state laser diodes. In this realization a plurality of such sources are placed on a stage which rotates the laser into the optical path allowing the sample to be illuminated sequentially by different wavelength laser light. Alternatively, mirrors or a fiber optic switch may be used to select the illuminating source.

Illuminator Made from a Filtered Broad-band Source

A broad-band source, such as a lamp, may be passed through a filter to illuminate the sample with a range of wavelengths much smaller than that of the unfiltered source. The filtered can be tuned, by changing its orientation, for example, or different filters can be rotated into place so as to provide for illuminating the sample at more than one wavelength band.

In one implementation, source 102 is a laser operating at a pulse rate of 5-10 kHz and an adjustable wavelength of 233 to 320 nm and an average power of 10-100 mW. The fundamental approach for building such a laser is to generate 700-960 nm VIS-NIR laser light with a tunable solid state laser, operating at 5-10 kHz, and to triple its output to the DUV 233-320 nm using third-harmonic-generation crystals. In other implementations, source 102 could be one or more lamps, or diodes, as discussed above, each operating at a different wavelength or filtered to output specific wavelengths. In still another embodiment, source 102 can be a wide spectrum lamp or diode whose output is sequentially adjusted using a monochromator to produce a time sequence of narrow band illumination.

Spectrum Detection

Emission spectrum detector 106 is selected for its sensitivity in the desired spectral range of the emitted radiation, and may be a spectrometer and detector such as the model HR2000, manufactured by Ocean Optics. In one embodiment spectrometers with rotatable gratings are used to enable synchronization of the wavelength range being measured with the wavelength of the illuminating system. Also, rotatable gratings allow adjustment in which the illuminating wavelength does not impinge on the detector, thereby allowing the recording medium to measure the spectrum from the sample being detected without interference from the illuminating wavelength light. In another embodiment, a scanning monochromator coupled to a single-point detector such as a photomultiplier tube is used. Other suitable detectors 106 include one or more diode or photoelectric tube detectors. Yet another detector 106 is a filter, e.g. a narrow pass-band, tunable, holographic filter that can be used with a constant wavelength source 102.

Light from the sample can be coupled onto the spectrometer or monochromator slit using fiber optics such as a DUV sapphire or quartz fiber. In another embodiment the light collection optics consist entirely or primarily of reflective elements, such as—for example—a Cassegrain microscope, with cylindrical or parabolic focusing optics. The light delivery and signal collection component may also be a scanning mirror. A fundamental requirement for this component is that the organisms remain within the illuminating beam for the duration of the measurement.

Analysis

Processor 108, e.g. a microprocessor or PC programmed with the spectral data processing algorithm discussed below, may also control the source 102 and make decisions, such as dwell time at each frequency, request for resampling, sample cell control, sample cell ejection etc. A signal indicating a positive reading, species detected, and its concentration may be communicated onto a local screen or other display device or to a remote location via radio. The complete spectral data set can be transmitted upon request for re-examination by a human or for archiving at a remote location.

Processor 108 is programmed with a spectral data processing algorithm that combines the plurality of spectral measurement data into a composite spectrum by stringing the spectral measurement data end-to-end. In this manner, the measurement becomes a single vector where the components represent a response of the sample to illuminated wavelength. For all intents and purposes, once combined the composite spectrum is treated as a single measurement of the sample. The composite spectrum therefore includes the spectral measurement data resulting from the emitted radiation of not just the substance of interest but of the additional substances not of interest that may be present and that may tend to mask the signature of the substance of interest. No training data and no reference or baseline are required, as a suitable classification algorithm, e.g. principal components analysis (PCA), least squares fitting, or in a preferred embodiment a multispectral processor such as the Intelligent Hypersensor Processing System (IHPS), described in U.S. Pat. No. 6,038,344, Palmadesso et al., issued Mar. 14, 2000, and incorporated herein by reference, or the Compression of Hyperdata with ORASIS Multisegment Pattern Sets (CHOMPS), described in U.S. Pat. No. 6,167,156, Antoniades et al., issued Dec. 26, 2000, and incorporated herein by reference, or the "Efficient Near Neighbor Search (ENN-Search) Method For High Dimensional Data Sets With Noise", described in U.S. patent application Ser. No. 10/113,643, filed Mar. 29, 2002, and incorporated herein by reference, process the composite spectrum.

IHPS processes the outputs of multiple sensors, which in the case of the present invention is the measured spectral data, and forms a series of pattern vectors through the concatenation of the measured spectral data. The data is simultaneously sent to two separate processor "pipes", although, in some applications the Adaptive Learning Module would be run first on a series of measured spectra and then the Demixer Module would be run. The first is the Demixer Module, which decomposes each pattern vector into a convex combination of a set of fundamental patterns which are the constituents of the "mixture". The decomposition is accomplished using projection operations termed "filter vectors" generated by the second processor pipe termed the Adaptive Learning Module. In this manner, the signature pattern, containing and or representative of one constituent or a substance of interest, and which is masked by the presence of other substances' emitted radiation, is separated from the latter. A Library database of signatures of known substances is preferably employed in order that the signatures of the other substances are determined automatically by processor 108. Information detailing the identification of a substance of interest, and optionally information concerning other substances as well, is output to a display device, e.g. a portable video monitor or LCD screen, alarm, and/or a communication link as may be convenient for the user and the intended application.

CHOMPS is a collection of algorithms designed to optimize the efficiency of multispectral data processing systems. CHOMPS employs two types of algorithms, focused searching algorithms and compression packaging algorithms. The focused algorithms reduce the computational burden of the prescreening process by reducing the number of comparisons needed to decide whether data is redundant, by selecting only those exemplars likely to result in the exclusion of measured spectral data for the prescreener comparisons. The compression packaging algorithms employed by CHOMPS compress the volume of the data necessary to describe the substance of interest and the other substances present. These in combination with IHPS (or other suitable multispectral processors) lead to a compressed exemplar data set, although it should be understood that the compression is optional, that is, it may not be necessary for a selected application and is selectable based on the particular detector design desired and/or its intended application or end use.

The ENN search algorithm is based upon the CHOMPS algorithm, but it does not stop searching when a suitable match is found, but instead continues looking for a better match. Accordingly, it extends CHOMPS when searching the Library to find an even better match for the spectral signature or signatures of interest. Additionally, the technical method of the search is different than that used in CHOMPS.

The IHPS, CHOMPS, and ENN algorithms have methods for organizing data and allowing fast comparisons that may be used as preprocessors or for managing large libraries. All, or perhaps only some, of the base algorithms are necessary. IHPS/CHOMPS/ENN contain a well developed set of algorithms designed for fast processing. They provide indications of the presence and estimates of the concentration of the sample constituents. The limits of the algorithms are determined by the physics of the response of the system.

In applying a multispectral algorithm such as IHPS, CHOMPS, or ENN, there are two aspects to the processing of the data that is proposed to be collected. The first is identification of the constituents of a measured mixture. The second is the determination of the concentration of the specific constituent. The power to make these determinations comes from the large number of measurements that are made. Each measurement of an emitted wavelength (for each illumination wavelength) gives a clue as to the makeup of the mixture. As the number of measurements increase, with increasing number of illuminating wavelengths, the power to make determinations of material identification and concentration also increases. Additionally, the effects of noise decrease with the increasing number of measurements.

The measured spectra of the mixtures exist in a large dimensional space where the dimensionality can be as high as the number of measurements. However, the effective dimension (when noise is small or can be ignored) can be much lower—roughly the number of distinguishable constituents. By making many measurements the likelihood of finding a dimension that can be used to distinguish similar materials increases. The ability to increase the "contrast" between similar items depends ultimately on physical nature of the materials—there must be a sufficient difference somewhere and it must be measurable.

CHOMPS is designed to analyze hyperspectral imagery. However, the concepts readily transfer over to almost any spectroscopic technique. The general idea is that the mixtures measured are a linear convex combination of constituent materials. This allows the processing to be based on convex geometry. The linear model is sufficient in most cases even when the data exhibits nonlinear effects such as the exponential decay associated with varying water depths.

CHOMPS' algorithms are generally run sequentially. The algorithms process data from hyperspectral images and Raman spectroscopy images or point measurements. The spectra are considered as vectors of length n, where n is the number of wavelength channels of emitted light measured. Composite spectra are created by combining multiple spectra each associated with a different wavelength laser illumination. Of particular importance are the filter vector algorithm and the prescreener algorithm. The algorithms are very fast and the time to process the data is not a limiting factor in the practice of the invention.

The filter vector algorithm is able to determine the concentrations of a particular, known substance embedded in a complex background. Calculation of the filter vectors is very fast—a simple matrix inversion. The spectrum of a material is often referred to as an "endmember." The filters are "matched" to the endmember being sought within the current background. The filter vector approach is based on a linear least squares approach to determining the concentrations of the constituent endmembers, and in the linear least squares sense it is an optimal solution.

The prescreener algorithm can organize a very large spectral library in an optimal manner. Once this is done a measured spectrum, or an endmember, can be quickly matched to a library spectrum.

CHOMPS/IHPS/ENN can process data much faster that the instrument can measure them. As the number of measured spectra grow a good representation of the background space spanned by the spectra is determined, and the algorithm can differentiate the substance of interest, e.g. a dangerous pathogen, more easily. The algorithm can work entirely from library spectra, and thus do some level of identification on a single measured spectrum, but that is likely dependent on having information about the expected background material.

The substance of interest should have a significant effect on the measured spectrum. A material that is sub-pixel covers less than the entire physical extent of the measurement area, with other substances not of interest accounting for the rest of the spectral information. A convolution of the spectral difference of the substance of interest compared to the background and the coverage area of the substance within the measurement area determines the ability to determine the presence of the substance. This is akin to being able to see a bright orange cone against a black background compared to seeing something the same size that is dark grey.

In order to do identification as opposed to anomaly detection the algorithm being used should be effective against subpixel targets. Certain algorithms used for hyperspectral analysis are of limited value. These include most statistical approaches used for classifying spectra. Such approaches depend on having some "ground truth" associated with the data. The spectra are then classified based on their statistical similarity to the ground truth. Methods such as Principle Component Analysis (PCA) are widely used but are not substantially useful here, as the analysis does not produce physically meaningful (constituent's) spectra, but instead produces directions in the data that maximize the variance.

The class of algorithms to which CHOMPS, IHPS, and ENN belong provides improved spectral data processing capabilities for the applications described here. This class of algorithms follows the Linear Mixture Model (LMM); these handle subpixel mixing, produce physically meaningful endmember spectra, and can produce estimations of the concentration of each endmember. Pixel Purity, available with the commercial package called ENVI, manufactured by Research Systems Inc. is one such algorithm. Pixel Purity works by projecting the data against random vectors. The purest spectrum of each material is more likely than mixtures to be on the extreme ends of the projected data. By repeatedly projecting the data and counting the number of times it is extreme, the most pure spectra may be obtained. However, the number of projections needed goes at least linearly as the amount of material in the pixel increases. To find extremely subpixel material requires more projections than is desirable. Even when the most pure endmembers (albeit not purest) are found from within the data, the algorithm does not give estimations of the pure endmembers as CHOMPS does. Additionally, it does not have any library handling ability as CHOMPS does.

NFINDR, an algorithm manufactured by TRA, Inc., and which is comparable to CHOMPS in performance and has about the same processing speed, works by finding the largest volume simplex possible from the data. It, however, also experiences difficulties with extremely subpixel spectra. Also, it will not make an estimation of the endmember, but rather just use that spectrum contained within the data. And like PP, NFINDR does not have any library handling ability.

CHOMPS acquires the resulting spectra emitted by the bio agent or substance of interest from a sequential or stepped scan through many different excitation laser pulses as, perhaps, a 4-dimensional hyperspectral cube whose labels are:
(1) Excitation wavelength
(2) Emitted wavelength
(3) Spatial dimension
(4) Time dimension Into each of these labeled locations the emitted amplitude in inserted. All these measurements would compose a data set. This organization of the data is one possible way that might be used. Many others also exist. The signature spectra may then be compared as noted above to a similarly configured Library of signature spectra to identify the presence of a substance of interest. The Library in a preferred embodiment includes signature spectra distinguishing not just individual microorganisms but also different species and subspecies, as well as individual characteristics such as the age of a microorganism, its growth medium, or other such environmental factors. For example, different spectral signatures in the Library can include subspecies of *E. Coli, E. Coli* grown in different media, and *E. Coli* of different ages. Essentially, the Library should include measurements of any and all organisms that are known and differentiable by the measurements. Any characteristics of the organisms that would result in a differentiable measured composite spectrum should be included. It is also conceivable for the system to identify spectra as spectra that are not in the Library. This is done by noting that endmembers have no close match in the library. These spectra could be later analyzed to determine if they indeed represent new organisms and then added to the library for future use.

Spectra produced by the invention may also be used with a multispectral processor 108 such as IHPS in a non-scanning or limited wavelength mode, in that the illumination source 102 can be set to excite a sample at a smaller number of selected wavelengths, and due to the processing advantage of IHPS, IHPS with CHOMPS, ENN, or another suitable multispectral processor with or without CHOMPS, effectively identify a substance of interest in the presence of other substances better than prior art devices.

To test the demixing ability of CHOMPS, test composite spectra were constructed from individual spectra published in the literature. The data are of BC and EC (*Bacillus cereus, E Coli*) bacteria irradiated with laser light at 222, 231, 242, and 251 nm at very different times. The data were re-sampled to a 5 $cm^{-1}$ spacing and to improve the resolving ability of CHOMPS the spectra taken at the 4 incident illumination wavelengths were joined together to form a composite spectra (the length of which can be varied, e.g. up to 625 channels). Thus, the Raman-spectral signatures of BC and EC bacteria illuminated at 222, 231, 242, and 251 nm were strung together to create a "four wavelength fingerprint" of each type. The four-wavelength spectrum of one organism was then added to the four-wavelength spectrum of the other (the clutter) in different ratios to simulate a small amount of organism present in a larger background clutter. The limit of detection is influenced by the extent to which the agent signal is masked by signals from other organisms (clutter) and by random noise. The detector also performs in the presence of clutter and random noise. Different amounts of random noise were added to determine an achievable level of noise immunity. CHOMPS was then applied to see whether, and to what extent it can recover the correct amount of the test organism. The Signal to Noise (S/N) level is defined as the average of (signal/noise) in each channel. Mixtures were made on a sliding amount between a pure endmember to one with $3\times10^{-3}$. With the endmembers known the filter vectors were calculated and applied to the mixtures. The results are shown in FIGS. 6*a-c*. On the y-axis is plotted 1 minus the difference between the expected answer and that found by applying the filter vectors. On the x-axis is expected amount. If the retrieval worked perfectly, the expected retrieved amounts would be the same and the y-axis would be 1.0 for all values of the x-axis. However, note that as the amount of the material becomes small the retrieved amount differs from the expected amount by an increasingly larger amount. The average S/N for the three graphs is 2, 37, and 450, as labeled for FIGS. 6*a-c*, respectively. FIG. 7 shows the noise level for the mixture and the mixture with noise added, for a S/N of 37, that is, for an original measured spectrum and the spectrum plus a normally distributed noise. FIG. 8 shows the results found when only using one of the illuminating laser wavelengths. FIG. 9 shows the result found when using two of the illuminating wavelengths. FIG. 10 shows the result found using all four of the illuminating wavelengths.

The results demonstrate that the amount of BC organism hidden among EC organisms in the ratio of 1/1000, equivalent to 100 agents among 100,000 other organisms, was correctly determined (with an error of 15%) using 4 illumination wavelengths with a signal to noise of 450. This is considered to be a very good result.

Good signal-to-noise ratios are important for lowering detection thresholds. For 100 illumination wavelengths, one can identify an agent hidden in clutter in a ratio much smaller than 1/1000. This is because, with 100 illumination wavelengths, the stated results improve at a minimum of by the square root of 100/4, or a factor of 5. All else being equal, one can expect to identify an organism hidden in clutter in the ratio of 1/1000 for signal to noise ratios of 450 and 37 (accuracy of 3%, 30%). The signal-to noise typical of resonant Raman is $10^3$-$10^4$, which is 2 to 22 better than used in the calculation. With illumination at 100 wavelengths not only does the influence of random noise decrease, but also the "contrast" or distinguishability between the organisms' patterns sharply increases. Other known mathematical techniques to reduce the effects of random noise mathematically may also be employed.

The detector 100 is well suited for continuous autonomous operation with occasional down-time for maintenance only. The performance of the system may be monitored remotely and continuously by, for example, monitoring for the presence and density of harmless species commonly found in the ambient background. Illuminator performance may be monitored with standard power meters and the results transmitted to the control computer. Standard electric power is the only consumable required.

In the scanned wavelength implementation, the detector 100 can physically scan through multiple wavelengths with a selected dwell time, e.g. of ~1 second, at each illumination wavelength. The processing/analysis such as with CHOMPS is fast, on the order of a few milliseconds. The apparatus can, therefore, complete an entire scan and analyze the spectral results in just minutes, or less, depending on the number of wavelengths measured and the particular implementation. Also, as discussed above, the apparatus can also be optionally used to scan at just a few or at one select frequency, if desired, and it should be understood that the number of scanned frequencies may be as high or as low as the designer and/or experimenter may choose depending on the particular application. The resolution of the spectral measurements may also be adjusted by balancing the conflicting requirements posed by the amount of photons the sample emits with the similarity of the spectra from the sample to be identified to spectra of other materials present. Higher resolution measurements require that the sample emit more photons. Lower resolution spectra require that the sample spectrum differ from spectra of other materials at the measured resolution. To identify organisms whose spectra are presented in figures in this application we expect to need a resolution of 1 to 50 wavenumbers ($cm^{-1}$). In other applications, or for other organisms, identification may possibly be made with much poorer spectral resolution—including resolution so poor that the measurement can be made with filtered photodetectors instead of with a spectrometer. In some applications the sample material to be identified may be chemically bound to another substance to produce a new material whose spectral signature is unique and/or very different from the signatures of other substances that may be present. In that case a measurement with poor spectral resolution may be possible. Applications in which substances have similar spectra may require better spectral resolution to detect subtle differences in the spectra.

The detector analyzes simultaneously for all the agents in its library. The number of organisms that the detector can distinguish is equal to the number of distinct hyperspectral fingerprints that are produced by illumination at multiple (e.g. 100) wavelengths. The four wavelengths spectra of EC and BC bacteria discussed above, for example, were found to differ from each other by 80 times the minimum that the CHOMPS algorithms require for identification. The difference increases further when 100 wavelengths instead of four are used. In fact, if agents differed from each other in spectra produced at one illuminations wavelength only, and were otherwise identical, the detector can distinguish 100 organisms. The number of false positives can be significantly reduced by repeating a measurement, since the detecting method need not damage the organism in the sample.

As discussed above, the invention is able to identify a particular species within a genus of a microbiological organism, e.g. to distinguish a pathogenic *E-coli* 157 from other harmless *E-coli* spectra fingerprints. Features of agent spectral fingerprints will vary based on the organism's stage of development and growth history. However, there is good evidence from traditional resonance Raman studies that spectral signatures from certain unique proteins/markers remain unaffected by the organism's growth stage of growth history. The detector can isolate this information and use it to provide important epidemiological and forensic information. Additionally, the processing algorithm can be programmed to ignore particular individual measurements with in the composite spectrum. This may be done to facilitate the determination of particular characteristics of the sample.

Although the examples provided herein are directed to resonant or near Raman data performed on bacteria, the apparatus can also identify proteins, viruses, cells, and organic and non-organic chemicals. Accordingly, the detector 100 can identify Category A, B, and C microorganisms or agents as defined by the Centers for Disease Control. Category A includes anthrax (*Bacillus anthracis*), botulism (*Clostridium botulinum* toxin), plague (*Yersinia pestis*), smallpox (*variola major*), tularemia (*Francisella tularensis*), and viral hemorrhagic fevers (filoviruses [e.g., Ebola, Marburg] and arenaviruses [e.g., Lassa, Machupo]). Category B includes brucellosis (*Brucella* species), epsilon toxin of *Clostridium perfringens*, food safety threats (e.g., *Salmonella* species, *Escherichia coli* O157:H7, *Shigella*), glanders (*Burkholderia mallei*), melioidosis (*Burkholderia pseudomallei*), psittacosis (*Chlamydia psittaci*), Q fever (*Coxiella burnetii*), ricin toxin from *Ricinus communis* (castor beans), staphylococcal enterotoxin B, typhus fever (*Rickettsia prowazekii*), viral encephalitis (alphaviruses [e.g., Venezuelan equine encephalitis, eastern equine encephalitis, western equine encephalitis]), and water safety threats (e.g., *Vibrio cholerae, Cryptosporidium parvum*). Category C includes emerging infectious diseases such as Nipah virus and hantavirus. Other possible sources include substances of human origin such as blood, feces, and spit in situations such as border control, hospital triage, and epidemics and group or mass infections of the civilian and/or military sectors. These can be identified in the environment at fixed sites, e.g. as a fixed installation of a detector 100 to monitor the air, water, containers, mail, AC/heating ducts, arenas, airport screening/security, and various surfaces, as well as in mobile or transient applications, e.g. as a human-portable or hand-held implementation of detector 100 or one mounted in a land vehicle or in an air or sea platform/vehicle. Detector 100 may further be used to verify the effectiveness of monitoring of decontamination procedures and processes.

The mathematical upper limit of distinguishability is that the composite spectra differ from each other in at least one measurement. Each composite spectrum consists of about 1000 measurements/illumination wavelength*100 illumination wavelengths=$10^5$ measurements. Thus, mathematically, in this example more than to $10^5$ agents can be distinguished, so that the mathematics of the detector are not the limiting factor for distinguishability.

The preferred detector embodiment uses no consumables and requires no pre-enrichment. The detector output lends itself naturally to wireless transmission. A wireless communication package is straight-forward to attach to the detector. Analyzed detector output can be presented in terms of the type and numbers of organisms detected combined with an alarm if any of these are harmful. Raw data can also be transmitted to a remote site for further analysis by specialists or for archiving. Triggers, external commands, diagnostic signals, etc. are likewise straight-forward to implement.

The apparatus can be a modular system, with the illuminator, analysis and communications packages, and the sampling unit separated by many meters. All the modules combined could occupy a volume of <3 cubic feet. No special logistical or environmental requirements exist.

Figure 11:
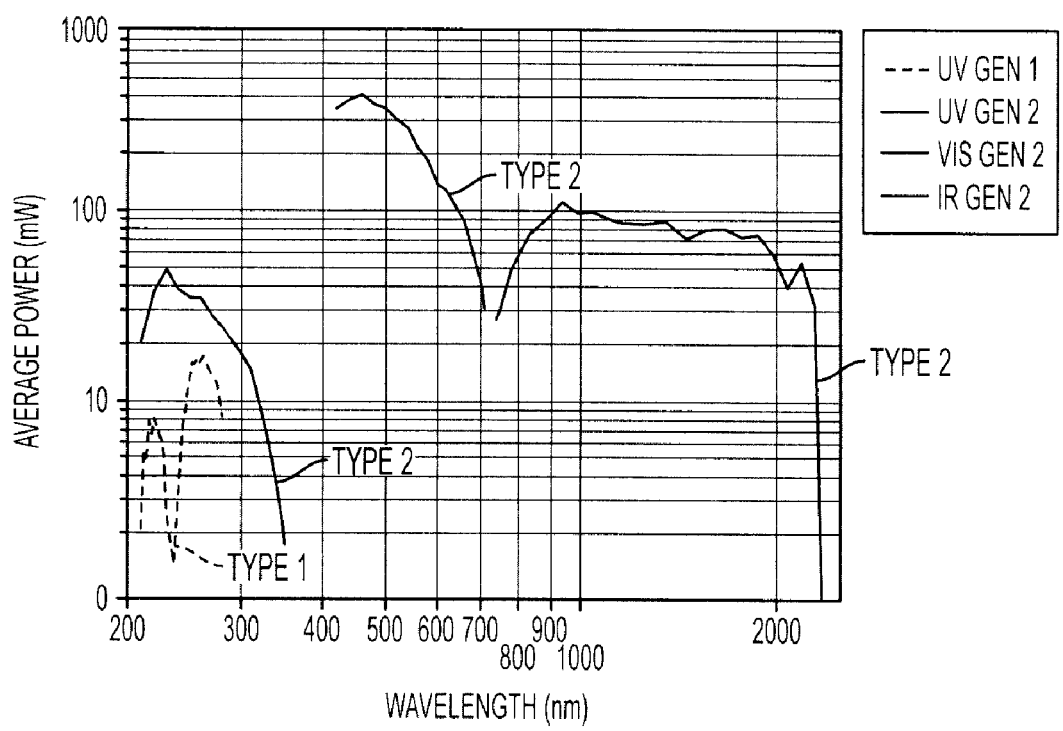
FIG. 11 is a graph showing average power vs. wavelength for a type 1 laser source and a type 2 laser source according to the invention.

Employing a type 1 source 102 as described above, 2-D spectral signatures of analytes were obtained, including microorganisms, TNT, MDX, HMX, PETN, diesel fuel vapor, fertilizer (ammonium nitrate vapor), solvents, and water. FIG. 11 is a graph showing average power vs. wavelength for a type 1 laser source and a type 2 laser source.

Obviously many modifications and variations of the present invention are possible in the light of the above teachings. For example, it should be evident from the above description that the invention can be applied to identifying a substance either in the presence of one or more other substances or without another substance present, e.g. in a pure culture. It is therefore to be understood that the scope of the invention should be determined by referring to the following appended claims.

We claim:

1. A method of identifying a substance, comprising:
   illuminating the substance with a laser output from a tunable light source to thereby induce the emission of radiation characteristic of the substance being illuminated;
   measuring the emitted radiation to obtain a plurality of spectral measurement data;
   inputting said spectral measurement data into a processor, said processor including a processing algorithm configured for:
   combining the plurality of spectral measurement data into a composite spectrum; and
   applying said algorithm to said composite spectrum whereby at least one parameter characteristic of the substance is identified while information in said composite spectrum contributed by an emission of radiation from any other substance is removed to thereby identify the presence of the substance.

2. A method as in claim 1, wherein the tunable light source is a continuously tunable, optical parametric oscillator laser.

3. A method as in claim 1, wherein the processing algorithm includes a multispectral data processing algorithm for analyzing multispectral data.

4. A method as in claim 3, wherein the multispectral data processing algorithm is Intelligent Hypersensor Processing System (IHPS).

5. A method as in claim 1, wherein the plurality of spectral measurement data comprises multiple measurements of emitted radiation at a resolution lower than 0.1 $cm^{-1}$.

6. A method as in claim 5, wherein the processing algorithm includes a multispectral data processing algorithm for analyzing multispectral data.

7. A method as in claim 6, wherein the multispectral data processing algorithm is Intelligent Hypersensor Processing System (IHPS).

8. A method as in claim 7, wherein the multispectral data processing algorithm correlates the multispectral data to spectral characteristics of the first substance and filters out spectral data from said at least one other substance.

9. A method as in claim 8, wherein the correlation is accomplished by comparing the multispectral data to spectral characteristics of substances in a spectral library database.

10. A method as in claim 1, wherein the illuminating is with radiation in the ultraviolet wavelength range.

11. A method of identifying the presence of a first substance in the presence of at least one other substance. comprising:

illuminating said first substance and said at least one other substance with a laser output from a tunable light source to thereby induce the emission of radiation characteristic of the substance being illuminated;

measuring the emitted radiation to obtain a plurality of spectral measurement data; and inputting said spectral measurement data into a processor, said processor including a multispectral data processing algorithm for identifying at least one parameter characteristic of said first substance while removing information contributed by an emission of radiation from said at least one other substance to thereby identify the presence of said first substance.

12. A method as in claim 11, wherein the tunable light source is a continuously tunable, optical parametric oscillator laser.

13. A method as in claim 11, wherein the multispectral data processing algorithm is Intelligent Hypersensor Processing System (IHPS).

14. A method as in claim 13, wherein the multispectral data processing algorithm correlates the multispectral data to spectral characteristics of the first substance and filters out spectral data from said at least one other substance.

15. A method is in claim 14, wherein the correlation is accomplished by comparing the multispectral data to spectral characteristics of substances in a spectral library database.

16. An apparatus for identifying the presence of a first substance in the presence of at least one other substance, comprising:

a tunable light source for illuminating the first substance and the at least one other substance to thereby induce the emission of radiation;

means for measuring the emitted radiation at a plurality of emission wavelengths to obtain a plurality of spectral measurement data; and a processor for processing said spectral measurement data, said processor including a multispectral data processing algorithm for identifying at least one parameter characteristic of said first substance while removing information in said spectral data contributed by an emission of radiation from said at least one other substance to thereby identify the presence of said first substance.

17. An apparatus as in claim 16, wherein the tunable light source is a continuously tunable, optical parametric oscillator laser.

18. An apparatus as in claim 16, wherein the tunable light source is a tunable laser.

19. An apparatus as in claim 16, wherein the multispectral data processing algorithm correlates the multispectral data to spectral characteristics of the first substance and filters out spectral data from said at least one other substance.

20. An apparatus as in claim 19 wherein the correlation is accomplished by comparing the multispectral data to spectral characteristics of substances in a spectral library database.

21. An apparatus as in claim 16, wherein the illuminating is with radiation in the ultraviolet wavelength range.

22. An apparatus as in claim 16, wherein the plurality of spectral measurement data comprises multiple measurements of emitted radiation at a resolution of lower than 0.1 cm$^{-1}$.

* * * * *